US012280036B2

(12) United States Patent
Leof et al.

(10) Patent No.: US 12,280,036 B2
(45) Date of Patent: Apr. 22, 2025

(54) USING FATTY ACID SYNTHASE INHIBITORS TO TREAT FIBROSIS

(71) Applicant: Mayo Foundation for Medical Education and Research, Rochester, MN (US)

(72) Inventors: Edward B. Leof, Rochester, MN (US); Ruth Lupu, Rochester, MN (US); Jeong-Han Kang, Rochester, MN (US); Mi-Yeon Jung, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 17/673,518

(22) Filed: Feb. 16, 2022

(65) Prior Publication Data

US 2022/0313654 A1 Oct. 6, 2022

Related U.S. Application Data

(63) Continuation of application No. 16/086,798, filed as application No. PCT/US2017/023549 on Mar. 22, 2017, now abandoned.

(60) Provisional application No. 62/311,615, filed on Mar. 22, 2016.

(51) Int. Cl.
| | |
|---|---|
| *A61K 31/277* | (2006.01) |
| *A61K 31/341* | (2006.01) |
| *A61K 31/365* | (2006.01) |
| *A61K 31/713* | (2006.01) |
| *A61P 11/00* | (2006.01) |
| *A61P 43/00* | (2006.01) |
| *C12N 15/113* | (2010.01) |

(52) U.S. Cl.
CPC .......... *A61K 31/365* (2013.01); *A61K 31/341* (2013.01); *A61K 31/713* (2013.01); *A61P 11/00* (2018.01); *A61P 43/00* (2018.01); *C12N 15/1137* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | | | |
|---|---|---|---|---|
| 6,414,026 | B1 * | 7/2002 | Billingham | A61P 1/16 514/567 |
| 6,887,853 | B2 * | 5/2005 | Strehlow | A61K 31/395 514/183 |
| 6,905,684 | B1 | 6/2005 | Kuwano | |
| 7,026,287 | B2 * | 4/2006 | Cantor | A61K 38/17 530/387.5 |
| 7,323,495 | B2 | 1/2008 | Terrero | |
| 7,767,700 | B2 * | 8/2010 | Bradford | A61P 1/16 514/345 |
| 7,820,682 | B2 | 10/2010 | Terakado et al. | |
| 7,956,088 | B2 | 6/2011 | Terrero | |
| 7,972,785 | B2 | 7/2011 | Hsieh et al. | |
| 8,048,912 | B2 * | 11/2011 | Gong | A61P 11/00 549/404 |
| 8,124,645 | B2 | 2/2012 | Terakado et al. | |
| 8,383,823 | B2 * | 2/2013 | Gant | C07B 59/002 546/290 |
| 8,455,456 | B2 | 6/2013 | Yu et al. | |
| 8,658,167 | B2 * | 2/2014 | Smith | A61P 17/02 424/152.1 |
| 2004/0021480 | A1 | 2/2004 | Doherty et al. | |
| 2004/0214804 | A1 | 10/2004 | Gulve et al. | |
| 2010/0190856 | A1 * | 7/2010 | Colomer Bosch | C07D 401/12 514/544 |
| 2010/0197708 | A1 | 8/2010 | Talley et al. | |
| 2015/0157634 | A1 | 6/2015 | Blazar et al. | |
| 2019/0070145 | A1 | 3/2019 | Leof et al. | |

FOREIGN PATENT DOCUMENTS

| | | |
|---|---|---|
| CA | 2309598 | 5/1999 |
| EP | 1029550 | 8/2000 |
| WO | WO 1999/058150 | 11/1999 |
| WO | WO 2002/000646 | 1/2002 |
| WO | WO 2007/048027 | 4/2007 |
| WO | WO 2008/039327 | 4/2008 |
| WO | WO 2008/106563 | 9/2008 |
| WO | WO 2013/173307 | 11/2013 |

OTHER PUBLICATIONS

Kang et al. (Defective fatty acid oxidation in renal tubular epithelial cells has a key role in kidney fibrosis development. Nat Med 21, 37-46 (2015)).*
Makarev et al. (Common pathway signature in lung and liver fibrosis. Cell Cycle. Jul. 2, 2016;15(13):1667-73).*
Andrianifahanana et al., "Profibrotic TGFβ responses require the cooperative action of PDGF and ErbB receptor tyrosine kinases," FASEB. J., 27(11):4444-54, Nov. 2013.
Ashley et al., "Targeting Inhibitor of Apoptosis Proteins Protects from Bleomycin-Induced Lung Fibrosis," Am. J. Respir. Cell Mol. Biology, 54(4):482-492, Apr. 2016.
Atabai et al., "Loss of Fatty Acid Synthase Increases the Severity of Lung Fibrosis by Preventing Collagen Resorption," QJM, Sep. 11, 2016, 109(suppl_1):S20-S21.
Ban et al., "Fibrosis in diabetes complications: pathogenic mechanisms and circulating and urinary markers," Vasc. Health Risk Manag., 4(3):575, Jun. 2008.

(Continued)

*Primary Examiner* — Layla Soroush
(74) *Attorney, Agent, or Firm* — Fish & Richardson P.C.

(57) ABSTRACT

This document relates to materials and methods for treating fibrosis (e.g., pulmonary fibrosis). For example, this document provides methods for using one or more fatty acid synthase (FASN) inhibitors to treat a mammal having fibrosis (e.g., pulmonary fibrosis), and/or a complication associated with fibrosis (e.g., hypoxia caused by pulmonary fibrosis).

5 Claims, 10 Drawing Sheets

(56) References Cited

OTHER PUBLICATIONS

Broderick et al. (Abstract CT203: Report of a first-in-human study of the first-in-class fatty acid synthase (FASN) inhibitor TVB-2640. Aug. 2015.vol. 75, Issue 15 Supplement.
Brusselmans et al., "Epigallocatechin-3-gallate is a potent natural inhibitor of fatty acid synthase in intact cells and selectively induces apoptosis in prostate cancer cells," Int. J. Cancer, Oct. 10, 2003, 106(6):856-862.
Canbay et al., "Fas enhances fibrogenesis in the bile duct ligated mouse: a link between apoptosis and fibrosis," Gastroenterology, 123(4):1323-1330, Oct. 2002.
Chapman et al., "Reversal of TGFβ1-Driven Profibrotic State in Patients with Pulmonary Fibrosis," N. Engl. J. Medicine, Mar. 12, 2020, 382(11):1068-1070.
Chen et al., "4-methylene-2-octyl-5-oxotetrahydrofuran-3-carboxylic acid (C75), an inhibitor of fatty-acid synthase, suppresses the mitochondrial fatty acid synthesis pathway and impairs mitochondrial function," J. Biol. Chem., 289(24):17184-94, Jun. 2014.
European Supplementary Search Report in European Application No. dated Mar. 13, 2019.
Extended European Search Report in European Application No. 17771043.1 dated Jul. 11, 2019, 12 pages.
GenBank Accession No. AAA73576.1, "fatty acid synthase [*Homo sapiens*]," Aug. 1, 1995, 3 pages.
GenBank Accession No. AAH63242.1, "Fatty acid synthase [*Homo sapiens*]," Jul. 15, 2006, 3 pages.
GenBank Accession No. AAS09886.1, "fatty acid synthase [*Homo sapiens*]," Mar. 15, 2014, 3 pages.
GenBank Accession No. AY451392.1, "*Homo sapiens* fatty acid synthase mRNA, complete cds," Mar. 15, 2004, 3 pages.
GenBank Accession No. BC063242.1, "*Homo sapiens* fatty acid synthase, mRNA (cDNA clone MGC:60044 IMAGE:6172538), complete cds, " Jul. 15, 2006, 4 pages.
GenBank Accession No. EAW89745.1, "fatty acid synthase [*Homo sapiens*]," Mar. 23, 2015, 4 pages.
GenBank Accession No. NM_004104.4, "*Homo sapiens* fatty acid synthase (FASN), mRNA," Sep. 11, 2017, 8 pages.
GenBank Accession No. NP_001274687.1, "collagen alpha-6(IV) chain isoform 3 precursor [*Homo sapiens*]," Apr. 23, 2017, 4 pages.
GenBank Accession No. NP_001274688.1, "collagen alpha-6(IV) chain isoform 4 precursor [*Homo sapiens*]," Jun. 3, 2017, 4 pages.
GenBank Accession No. NP_001274689.1, "collagen alpha-6(IV) chain isoform 5 precursor [*Homo sapiens*]," Jun. 3, 2017, 4 pages.
GenBank Accession No. NP_001290039.1, "collagen alpha-1(IV) chain isoform 2 precursor [*Homo sapiens*]," Sep. 10, 2017, 3 pages.
GenBank Accession No. NP_001836.3, "collagen alpha-1(IV) chain isoform 1 preproprotein [*Homo sapiens*]," Sep. 10, 2017, 4 pages.
GenBank Accession No. NP_001838.2, "collagen alpha-6(IV) chain isoform A precursor [*Homo sapiens*]," Jun. 3, 2017, 4 pages.
GenBank Accession No. NP_001892, "connective tissue growth factor precursor [*Homo sapiens*]," Sep. 18, 2017, 3 pages.
GenBank Accession No. NP_004095.4, "fatty acid synthase [*Homo sapiens*]," Sep. 11, 2017, 6 pages.
GenBank Accession No. P02452, "RecName: Full-Collagen alpha-1(I) chain; AltName: Full=Alpha-1 type I collagen; Flags: Precursor," Sep. 7, 2016, 32 pages.
GenBank Accession No. P02751.4, "RecName: Full=Fibronectin; Short=FN; AltName: Full=Cold-insoluble globulin; Short=CIG; Contains: RecName: Full=Anastellin; Contains: RecName: Full= Ugl-Y1; Contains: RecName: Full=Ugl-Y2; Contains: RecName: Full=Ugl-Y3; Flags: Precursor," Aug. 30, 2017, 40 pages.
GenBank Accession No. P49327.3, "Send to: RecName: Full=Fatty acid synthase; Includes: RecName: Full=[Acyl-carrier-protein] S-acetyltransferase; Includes: RecName: Full=[Acyl-carrier-protein] S-malonyltransferase; Includes: RecName: Full=3-oxoacyl-[acyl-carrier-protein] synthase; Includes: RecName: Fu, "Aug. 30, 2017, 24 pages.
Huang et al., "Histone modifications are responsible for decreased Fas expression and apoptosis resistance in fibrotic lung fibroblasts," Cell Death Disease, 4(5):e621, May 2, 2013, 8 pages.
International Search Report in International Application No. PCT/US2017/023549, Jul. 17, 2018, 6 pages.
Jones and Infante, "Molecular Pathways: Fatty Acid Synthase," Clin. Cancer Res., 21(24):5434-38, Dec. 2015.
Kuwano et al., "The involvement of Fas-Fas ligand pathway in fibrosing lung diseases," Am. J. Respir. Cell Mol. Biology, 20(1):53-60, Jan. 1999.
Li et al., "Inhibition of connective tissue growth factor by siRNA prevents liver fibrosis in rats," J. Gene. Med., 8(7):889-900, Jul. 2006.
Loomba et al., "TVB-2640 (FASN Inhibitor) for the Treatment of Nonalcoholic Steatohepatitis: FASCINATE-1, a Randomized, Placebo-Controlled Phase 2a Trial," Gastroenterology, Jul. 23, 2021, 161(5):1475-1486.
Lopez et al., "Differential role of the Fas/Fas ligand apoptotic pathway in inflammation and lung fibrosis associated with reovirus 1/L-induced bronchiolitis obliterans organizing pneumonia and acute respiratory distress syndrome," J. Immunology, 183(12):8244-8257, Dec. 15, 2009.
O'Farrell et al. (Biomarker Analyses from Dose Escalation Phase of FASN Inhibitor TVB-2640 Phase 1 Study Shows Target Engagement in Solid Tumor Patients. [abstract]. In: Proceedings of the AACR-NCI-EORTC International Conference: Molecular Targets and Cancer Therapeutics; Nov. 5-9, 2015; Boston, MA. Philadelphia (PA.
Relat et al., "Different fatty acid metabolism effects of (-)-epigallocatechin-3-gallate and C75 in adenocarcinoma lung cancer," BMC cancer, 12(1):280, Dec. 2012.
Romero et al. (A pneumocyte-macrophage paracrine lipid axis drives the lung toward fibrosis. Am J Respir Cell Mol Biol. 2015;53(1):74-86.).
Sriram et al., "Enhancement of Antioxidant Defense System by Epigallocatechin-3-gallate during Bleomycin Induced Experimental Pulmonary Fibrosis," Biol. Pharm. Bulletin, Jul. 2008, 31(7):1306-1311.
Sriram et al., "Epigallocatechin gallate attenuates fibroblast proliferation and excessive collagen production by effectively intervening TGF-β1 signalling," Clin. Exp. Pharmacol. Physiology, Aug. 2015, 42(8):849-859.
Sriram et al., "Epigallocatechin-3-gallate augments antioxidant activities and inhibits inflammation during bleomycin-induced experimental pulmonary fibrosis through Nrf2-Keap1 signaling," Pulm. Pharmacol. Therapeutics, Jun. 2009, 22(3):221-236.
Wang et al., "Attenuation of fibrosis in vitro and in vivo with SPARC siRNA," Arthritis research & therapy, 12(2):R60, Apr. 2010.
Zisman et al., "Pulmonary Fibrosis," Fibrosis Research, pp. 3-44, 2008.

\* cited by examiner

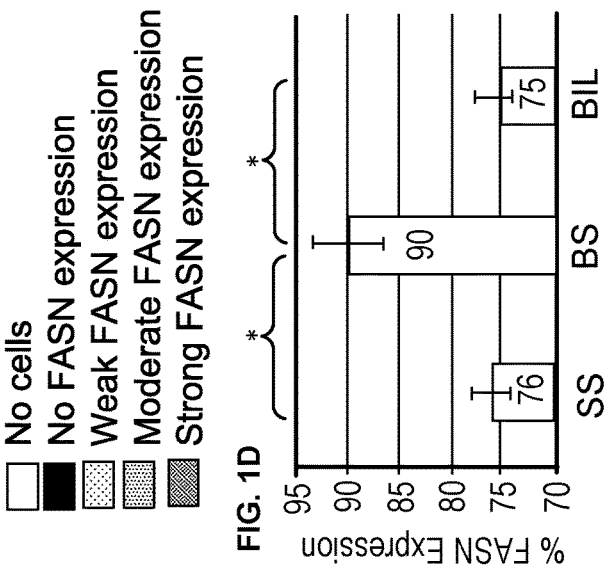
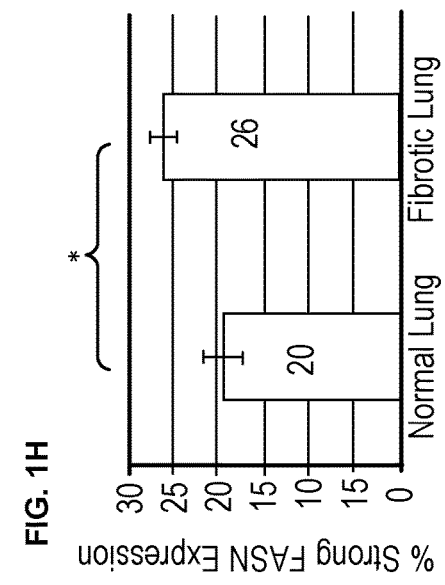
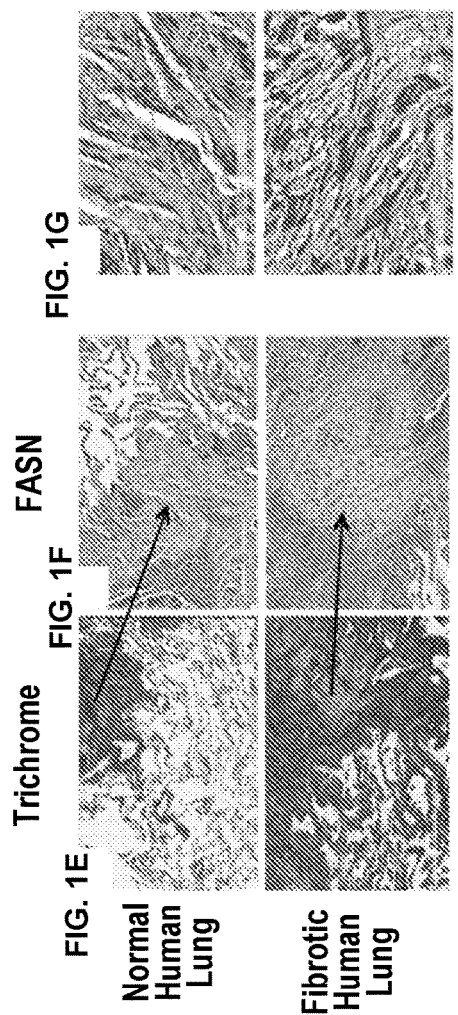

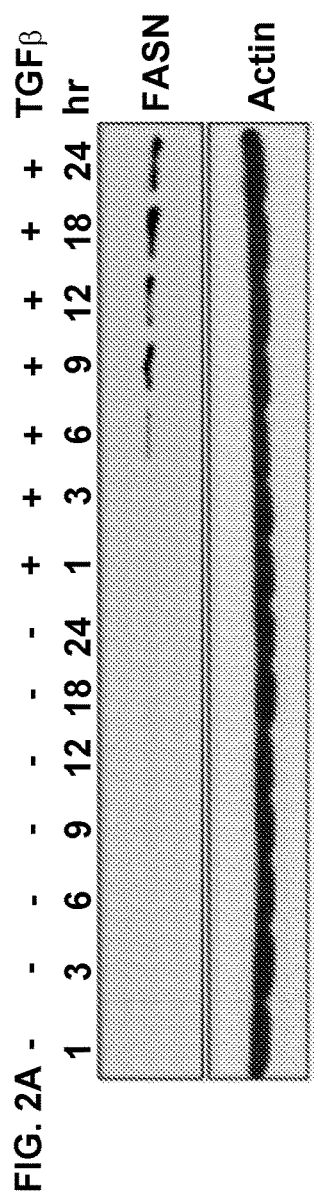
FIG. 2A
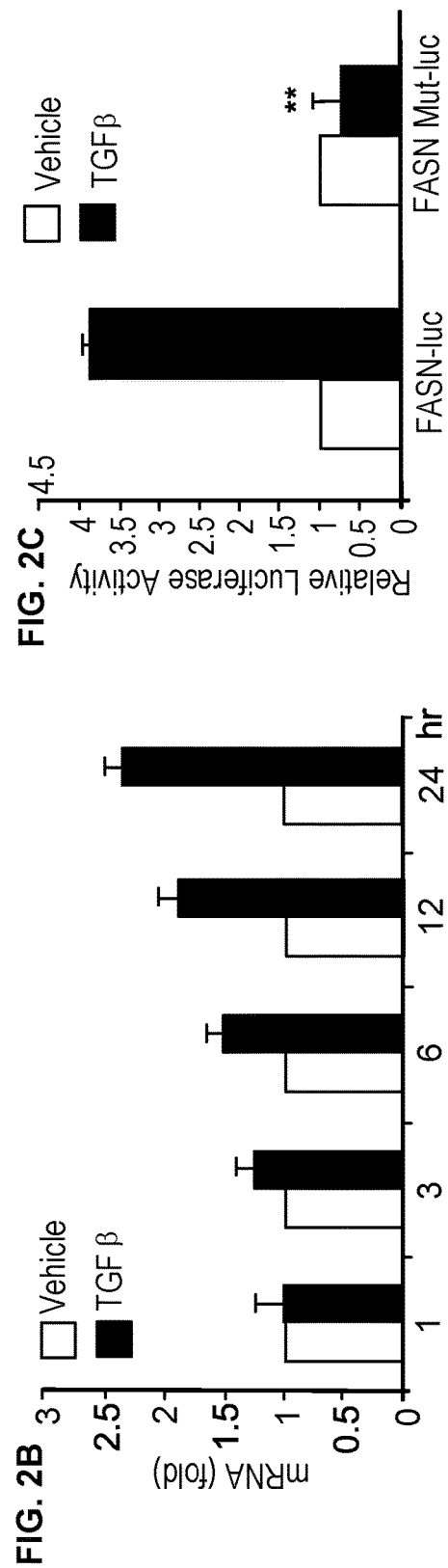
FIG. 2B
FIG. 2C
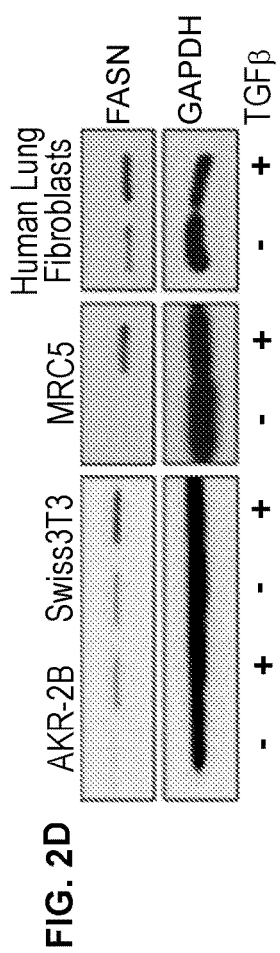
FIG. 2D

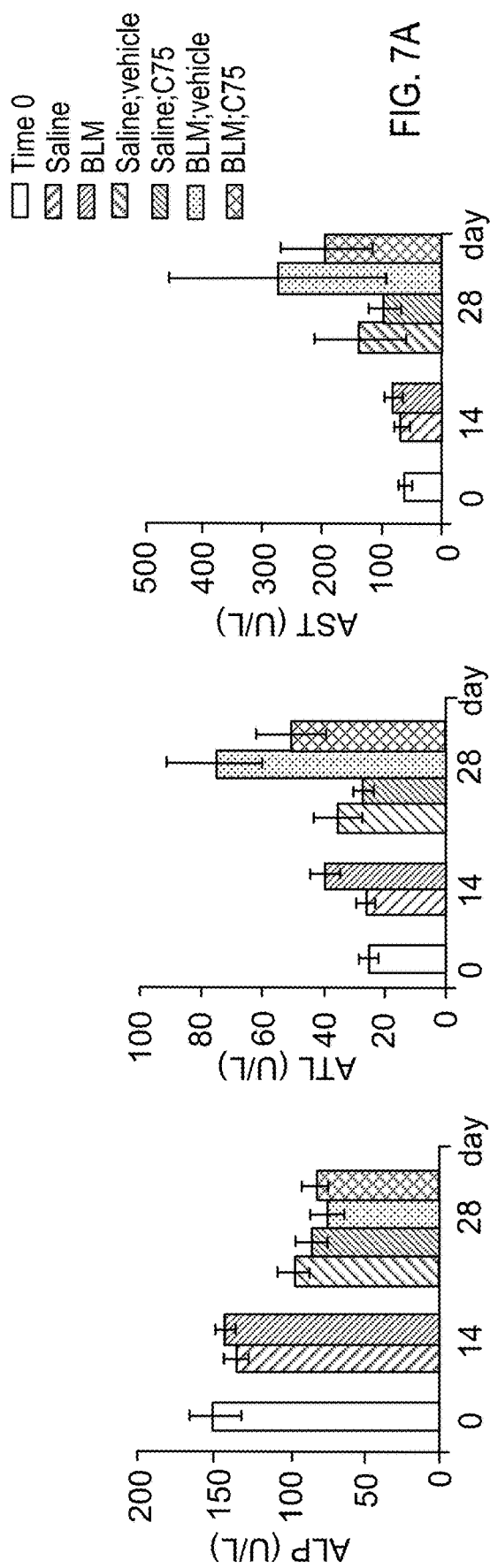
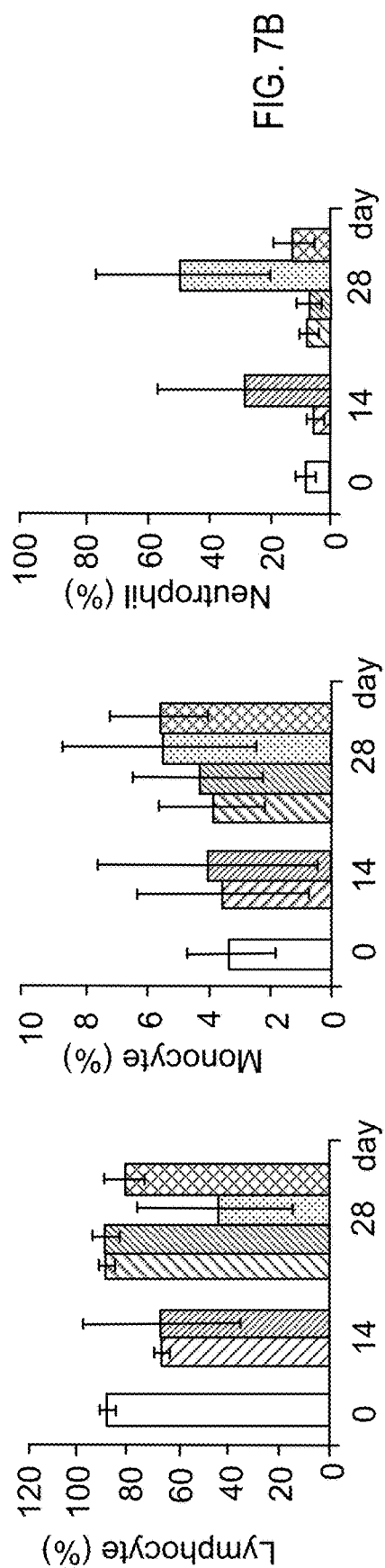
FIG. 7A
FIG. 7B

USING FATTY ACID SYNTHASE INHIBITORS TO TREAT FIBROSIS

CROSS-REFERENCE TO RELATED APPLICATIONS

This application is a continuation of U.S. Utility application Ser. No. 16/086,798, filed on Sep. 20, 2018, which is a National Stage Application under 35 U.S.C. § 371 that claims the benefit of Application Serial No. PCT/US2017/023549 filed on Mar. 22, 2017, which also claims the benefit of U.S. Provisional Application Ser. No. 62/311,615, filed on Mar. 22, 2016. The disclosures of the prior applications are considered part of (and are incorporated by reference in) the disclosure of this application.

STATEMENT AS TO FEDERALLY SPONSORED RESEARCH

This invention was made with government support under GM054200 and GM055816 awarded by the National Institutes of Health. The government has certain rights in the invention.

BACKGROUND

1. Technical Field

This document relates to materials and methods for treating fibrosis (e.g., pulmonary fibrosis). For example, this document provides methods for using one or more fatty acid synthase (FASN) inhibitors to treat a mammal having fibrosis (e.g., pulmonary fibrosis), and/or a complication associated with fibrosis (e.g., hypoxia caused by pulmonary fibrosis).

2. Background Information

Fibrosis is the formation of excess fibrous connective tissue in an organ or tissue in a reparative or reactive process. Fibrosis can damage the architecture and function of the underlying organ or tissue. For example, pulmonary fibrosis occurs when lung tissue becomes damaged and scarred, making it difficult for your lungs to work properly. Pulmonary fibrosis affects 200,000 people in the US, with an estimated 48,000 new cases are diagnosed each year (National Institutes of Health web page (www.nhlbi.nih.gov), 2010). Pulmonary fibrosis has a median survival rate of just two to three years, and more than ⅔ of patients will die within five years. There is no known cause and no cure for pulmonary fibrosis.

SUMMARY

This document provides materials and methods for treating fibrosis (e.g., pulmonary fibrosis), and/or a complication associated with fibrosis (e.g., hypoxia caused by pulmonary fibrosis). For example, this document provides methods and materials for administering one or more FASN inhibitors to a mammal having fibrosis (e.g., pulmonary fibrosis) under conditions wherein the severity of fibrosis is reduced. A FASN inhibitor can be an inhibitor of FASN polypeptide expression or an inhibitor of FASN polypeptide activity.

As demonstrated herein, FASN inhibitors can be effective to treat fibrosis and/or a complication associated with fibrosis. In some cases, one or more FASN inhibitors can be used to reduce the symptoms of fibrosis and/or a complication associated with fibrosis. In some cases, one or more FASN inhibitors can be used to decrease expression of profibrotic genes, to improve peripheral blood oxygenation, and/or to increase lung hydroxyproline content.

In general, one aspect of this document features a method for treating fibrosis in a mammal. The method includes, or consists essentially of, administering an inhibitor of FASN to a mammal identified said mammal as having fibrosis, wherein a symptom of said fibrosis is reduced. The mammal can be a human. The inhibitor can be C75. The inhibitor can be a FASN-targeting siRNA. The fibrosis can be pulmonary fibrosis (e.g., idiopathic pulmonary fibrosis).

In another aspect, this document features a method for treating a complication associated with fibrosis in a mammal. The method includes, or consists essentially of, administering an inhibitor of fatty acid synthase activity to a mammal identified said mammal as having a complication associated fibrosis, wherein a symptom of said complication is reduced. The mammal can be a human. The inhibitor can be C75. The inhibitor can be a FASN-targeting siRNA. The fibrosis can be pulmonary fibrosis (e.g., idiopathic pulmonary fibrosis). The complication associated with fibrosis can be hypoxia.

In another aspect, this document features a method for increasing polypeptide expression in cells. The method includes, or consists essentially of, contacting the cells with an inhibitor of fatty acid synthase activity, wherein expression of one or more profibrotic genes is decreased. The cells can be human cells. The cells can be lung cells. The inhibitor can be C75. The inhibitor can be a FASN-targeting siRNA. The one or more profibrotic genes can be selected from profibrotic genes collagen I, collagen IV, fibronectin, connective tissue growth factor, and alpha smooth muscle actin.

In another aspect, this document features a method for improving peripheral blood oxygenation in a mammal. The method includes, or consists essentially of, administering an inhibitor of FASN to a mammal identified a mammal, wherein peripheral blood oxygenation is increased in the mammal. The mammal can be a human. The inhibitor can be C75. The inhibitor can be a FASN-targeting siRNA.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1H show FASN expression in mouse and human lung tissue. FIGS. 1A-1C are histological sections of non-fibrotic (Saline:Saline (SS), A-C top), fibrotic (Bleomycin:Saline (BS), A-C middle), and fibrosis dual-treated with Imatinib and Lapatinib (Bleomycin:Imat+Lap (BIL) A-C bottom; which was previously shown to decrease pulmonary fibrosis, Andrianifahanana et al., 2013 *FASEB J* 27(11):

4444-54) mouse lungs stained with Masson's Trichrome (A), FASN antibodies co-stained with Hematoxylin (B), or color deconvoluted images (C). FIG. 1D is a graph of a quantification of FASN expression of non-fibrotic (SS), fibrotic (BS), and dual-treated (BIL) mouse lung tissues; SS to BS *p-value=0.021, and BS to BIL *p-value=0.025. FIGS. 1E-1F are histological sections of normal (E-G top), and fibrotic (E-G bottom) human lungs stained with Masson's Trichrome (E), FASN antibodies co-stained with Hematoxylin (F; arrows indicate normal fibroblasts (top), or fibrotic foci observed in IPF (bottom)), or color deconvoluted images (G). FIG. 1H is a graph of a quantification of FASN expression in human lung; *p-value=0.012.

FIGS. 2A-2D show that TGFβ regulates FASN expression in murine and human fibroblasts. FIG. 2A is a Western blot for FASN or actin (as a loading control) at the indicated times in the absence (−) or presence (+) of TGFβ. FIG. 2B is a graph of the amount of FASN mRNA at the indicated times in the absence (vehicle) or presence of TGFβ. FIG. 2C is a graph of relative luciferase activity in AKR-2B cultures transiently transfected with wild-type FASN (FASN-luc) or mutant FASN (FASN-Mut-luc) luciferase constructs; **p-value<0.01. FIG. 2D is a Western blot for FASN or GAPDH (as a loading control) in murine (AKR-2B and Swiss 3T3) and human (MRCS) lung fibroblast lines or primary human lung fibroblasts in the absence (−) or presence (+) of TGFβ.

FIG. 3A is a Western blot for FASN, pSmad2, pSmad3, connective tissue growth factor (CTGF), and GAPDH (loading control) in AKR-2B cells transfected with either a nontargeting (NT) control siRNA or with Smad2/3-targeting siRNA in the absence (−) or presence (+) of TGFβ. FIG. 3B is a Western blot for FASN, pSmad2, pSmad3, CTGF, and GAPDH (loading control) in MRCS cells transfected with either a nontargeting (NT) control siRNA or with Smad2/3-targeting siRNA in the absence (−) or presence (+) of 10 ng/ml TGFβ. FIG. 3C is a Western blot for FASN, pS6K, S6K, pErk, pSmad3, and GAPDH (loading control) in AKR-2B cells stimulated in the absence (−) or presence (+) of TGFβ plus LY294002, U0126, MK2206, Rapamycin, or Torin. FIG. 3D is a Western blot for FASN, pS6K, S6K, pErk, pSmad3, and GAPDH (loading control) in MRCS cells stimulated in the absence (−) or presence (+) of TGFβ plus LY294002, U0126, MK2206, Rapamycin, or Torin. FIG. 3E is a Western blot for FASN, Rictor, Raptor, mTOR, and GAPDH (loading control) in AKR-2B cells cultured in the absence (−) or presence (+) of non-targeting short hairpin RNAs (shNT) as a control, or shRNAs targeting mTOR, Raptor, or Rictor clones.

FIG. 4A is a Western blot for FASN, Collagen I (Col I), Collagen IV (Col IV), Fibronectin (FN), connective tissue growth factor (CTGF), pSmad3, and GAPDH (loading control) in murine AKR-2B or human lung MRCS fibroblasts treated with vehicle (−) or C75 in the presence (+) or absence (−) of TGFβ. FIG. 4B is a graph of soft agar colony formation by AKR-2B cells in the presence or absence of TGFβ (10 ng/ml) and the indicated C75 concentration; *p-value<0.05, **p-value<0.01. FIG. 4C shows scratch assays performed on AKR-2B or MRCS cells in the absence (Con) or presence of TGFβ and C75; red bands indicate the leading edge following 24 hours in the absence (Con) or presence of TGFβ and C75.

FIG. 5A is a Western blot for FASN, Collagen I (Col I), Collagen IV (Col IV), Fibronectin (FN), connective tissue growth factor (CTGF), pSmad3, and GAPDH (loading control) in AKR-2B or MRCS cells transfected with either a nontargeting (NT) control siRNA or with FASN-targeting siRNA in the absence (−) or presence (+) of TGFβ. FIG. 5B is a graph of soft agar colony formation by AKR-2B cells transfected with either a nontargeting (NT) control siRNA or with FASN-targeting siRNA in the absence (−) or presence (+) of TGFβ; **p-value<0.01. FIG. 5C shows scratch assays performed on AKR-2B or MRCS cells transfected with either a nontargeting (NT) control siRNA or with FASN-targeting siRNA in the absence (−) or presence (+) of TGFβ; red bands indicate the leading edge following 24 hr in the absence (−) or presence (+) of TGFβ.

FIG. 6A shows optical densities (at a wavelength of 570 nm; OD570) of AKR-2B cells grown in 0.1% FBS or 10% FBS, and MRCS cells grown in FBS free or 10% FBS, and treated with vehicle (0.1% DMSO), or C75 (3 μM). FIG. 6B shows cell counts for AKR-2B cells and MRCS cells grown in 0.1% FBS or 10% FBS, and MRCS cells grown in FBS free or 10% FBS, and treated with vehicle (0.1% DMSO), or C75 (3 μM).

FIGS. 7A-7B contain graphs showing FASN inhibition has no effect on murine liver enzymes or inflammatory cell recruitment. FIG. 7A shows serum levels (U/L, units per liter) of alkaline phosphatase (ALP), alanine aminotransferase (ALT), and albumin (AST) in mice challenged with bleomycin (BLM) or saline, and treated with vehicle or C75. FIG. 7B shows quantification of lymphocytes, monocytes, and neutrophils in mice challenged with bleomycin (BLM) or saline, and treated with vehicle or C75.

FIG. 10A is a graph of peripheral blood oxygen determined on days 21 (d21) and 35 (d35) in mice infected adenovirus particles expressing GFP (control) or TGFβ1, and treated with either vehicle or C75. FIG. 10B is a graph showing lung hydroxyproline content in mice infected adenovirus particles expressing GFP (control) or TGFβ1, and treated with either vehicle (−) or C75 (+). FIG. 10C is a graph of qPCR expression of alpha smooth muscle actin (α-SMA), collagen Iα1 (Col Iα1), and connective tissue growth factor (CTGF). *P<0.05, **P<0.01.

DETAILED DESCRIPTION

Figure 3A:
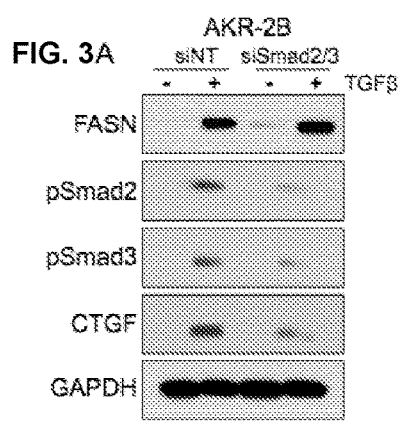
FIGS. 3A-3E show FASN induction by TGFβ is independent of pSmad2/3 and mediated via mTORC1 signaling.

This document provides methods and materials for treating fibrosis. For example, this document provides methods and materials for using FASN inhibitors to treat fibrosis (e.g., pulmonary fibrosis) and/or a complication associated with fibrosis (e.g., hypoxia caused by pulmonary fibrosis). In some cases, one or more FASN inhibitors can be used to reduce the symptoms of fibrosis. In some cases, one or more FASN inhibitors can be used to decrease expression of profibrotic genes and/or to improve peripheral blood oxygenation.

When treating fibrosis as described herein, the fibrosis can be in any tissue. Fibrosis can occur in many tissues within the body including, without limitation, lungs (pulmonary fibrosis; e.g., cystic fibrosis and/or idiopathic pulmonary fibrosis), liver (cirrhosis), heart (atrial fibrosis, endomyocardial fibrosis, old myocardial infarction), brain (glial scar), kidney (renal fibrosis; end stage renal diseases), ovary (ovarian cancer induced intestinal or peritoneal adhesions), and pancreas (pancreatitis). Other types of fibrosis include arthrofibrosis (knee, shoulder, other joints), Crohn's Disease (intestine), Dupuytren's contracture (hands, fingers), keloid (skin), mediastinal fibrosis (soft tissue of the mediastinum), myelofibrosis (bone marrow), Peyronie's disease (penis), nephrogenic systemic fibrosis (skin), progressive massive fibrosis (lungs), retroperitoneal fibrosis (soft tissue of the retroperitoneum), and scleroderma/systemic sclerosis (skin, lungs). In some embodiments, the fibrosis treated as described herein can be pulmonary fibrosis, such as idiopathic pulmonary fibrosis.

When treating a complication associated with fibrosis as described herein, the complication associated with fibrosis can be hypoxia caused by pulmonary fibrosis. Other complications associated with fibrosis include, without limitation, pain and organ failure.

In some cases, the materials and methods provided herein can be used to reduce the symptoms of fibrosis. Symptoms of pulmonary fibrosis include, without limitation, reduced shortness of breath, coughing, and diminished exercise tolerance.

In some cases, the materials and methods provided herein can be used to improve peripheral blood oxygenation.

In some cases, the materials and methods provided herein can be used to increase lung hydroxyproline content.

In some cases, the materials and methods provided herein can be used to decrease expression of profibrotic genes (e.g., Collagen I (Col I such as Col I$\alpha$1), Collagen IV (Col IV), Fibronectin (FN), connective tissue growth factor (CTGF), and alpha smooth muscle actin ($\alpha$-SMA)). Methods for decreasing expression of profibrotic genes in cells can include contacting the cells with one or more FASN inhibitors. Cells can be in vivo or in vitro. Cells can be from any appropriate sources (e.g., mammalian cells such as human cells). In addition, the cells can be any type of cell including, without limitation, lung, liver, heart, neurons, osteoclasts, osteoblasts, chondrocytes, intestinal (e.g., intestinal epithelial), and/or bone marrow (e.g., hemopoietic or stromal). One or more FASN inhibitors can be contacted with the cells by any appropriate method. For example, in humans, a composition containing one or more FASN inhibitor described herein can be used to decrease expression of a human Col I polypeptide, a human Col IV polypeptide, a human FN polypeptide, a human CTGF polypeptide, or a combination thereof. In some cases, a human Col I polypeptide can have an amino acid sequence set forth in, for example, National Center for Biotechnology Information (NCBI) Accession No: P02452 (see, e.g., GI No. 296439504). In some cases, a human Col IV polypeptide can have an amino acid sequence set forth in, for example, NCBI Accession Nos: NP_001836.3 (see, e.g., GI No. 734520330), NP_001290039.1 (see, e.g., GI No. 734520332), NP_001274687.1 (see, e.g., GI No. 567757600), NP_001274688.1 (see, e.g., GI No. 567757602), NP_001274689.1 (see, e.g., GI No. 567757604), NP_001838.2 (see, e.g., GI No. 148536823), and NP_001274687.1 (see, e.g., GI No. 567757600). In some cases, a human FN polypeptide can have an amino acid sequence set forth in, for example, NCBI Accession No: P02751.4 (see, e.g., GI No. 300669710). In some cases, a human CTGF polypeptide can have an amino acid sequence set forth in, for example, NCBI Accession No: NP_001892 (see, e.g., GI No. 4503123).

Any type of mammal having fibrosis (or a complication associated with fibrosis) or at risk for developing fibrosis (or a complication associated with fibrosis) can be treated as described herein. For example, humans and other primates such as monkeys having fibrosis can be treated with one or more FASN inhibitors. In some cases, dogs, cats, horses, cows, pigs, sheep, rabbits, mice, and rats can be treated with one or more FASN inhibitors as described herein.

Any appropriate method can be used to identify a mammal having fibrosis (or a complication associated with fibrosis) or as being at risk for developing fibrosis (or a complication associated with fibrosis). For example, imaging techniques (e.g., chest x-ray, computerized topography (CT) scan, echocardiogram), lung function test (e.g., pulmonary function test, oximetry, exercise stress test), and/or tissue sample analysis (e.g., bronchoscopy, bronchoalveolar lavage, surgical biopsy) can be used to identify a human or other mammal having fibrosis.

Once identified as having fibrosis (or a complication associated with fibrosis) or as being at risk for developing fibrosis (or a complication associated with fibrosis), the mammal can be administered or instructed to self-administer one or more FASN inhibitors (e.g., a composition containing one or more FASN inhibitors that reduce FASN polypeptide expression and/or activity).

A FASN inhibitor can be an inhibitor of FASN polypeptide expression or an inhibitor of FASN polypeptide activity. Examples of compounds that reduce FASN polypeptide activity include, without limitation, C75, orlistat, epigallocatechin-3-gallate (EGCG), triclosan, GSK837149A, GSK2194069, JNJ-54302833, IPI-9119, and TVB-2640 (Jones et al., 2015 Clin Cancer Res 21(24):5434-38). Examples of compounds that reduce FASN polypeptide expression include, without limitation, nucleic acid molecules designed to induce RNA interference (e.g., a small interfering RNA (siRNA) molecule or a short hairpin RNA (shRNA) molecule), antisense molecules, and miRNAs. Additional FASN inhibitors can be readily designed based upon the nucleic acid and/or polypeptide sequences of FASN. Examples of a FASN nucleic acids include, without limitation, the human FASN sequence set forth in GenBank® Accession Nos. AY451392.1 (see, e.g., GI No. 41584441), BC063242.1 (see, e.g., GI No. 38648666), and NM_004104.4 (see, e.g., GI No. 41872630). Examples of FASN polypeptides include, without limitation, the human FASN polypeptide having the amino acid sequence set forth in GenBank® accession Nos: AAA73576.1 (see, e.g., GI No. 915392), AAS09886.1 (see, e.g., GI No. 41584442), AAH63242.1 (see, e.g., GI No. 38648667), EAW89745.1 (see, e.g., GI No. 119610151), NP_004095.4 (see, e.g., GI No. 41872631), and P49327.3 (see, e.g., GI No. 269849686).

In some cases, one or more FASN inhibitors (e.g., one, two, three, four, five, or more FASN inhibitors) can be administered to a mammal to treat fibrosis (e.g., pulmonary fibrosis) and/or a complication associated with fibrosis (e.g., hypoxia caused by pulmonary fibrosis). For example, two or more FASN inhibitors can be administered to a mammal (e.g., a human with fibrosis) to treat fibrosis (e.g., pulmonary fibrosis).

A composition including one or more FASN inhibitors can be administered to a mammal having fibrosis (e.g., pulmonary fibrosis) and/or a complication associated with fibrosis as a combination therapy with one or more additional agents/therapies used to treat fibrosis. For example, a combination therapy used to treat a mammal having fibrosis can include administering to the mammal (e.g., a human) a composition including one or more FASN inhibitors and one or more fibrosis treatments such as medication (e.g., corticosteroid (e.g., prednisone), methotrexate, cyclosporine, acetylcysteine, pirfenidone, and/or nintedanib), oxygen therapy, pulmonary rehabilitation, and/or surgery (lung transplant).

In embodiments where one or more FASN inhibitors are used in combination with one or more additional agents used to treat fibrosis, the one or more additional agents can be administered at the same time or independently. For example, the composition including one or more FASN inhibitors can be administered first, and the one or more additional agents administered second, or vice versa. In embodiments where one or more FASN inhibitors are used in combination with one or more additional therapies used to treat fibrosis, the one or more additional therapies can be performed at the same time or independently of the administration of one or more FASN inhibitors. For example, the composition including one or more FASN inhibitors can be administered before, during, or after the one or more additional therapies are performed.

In some cases, one or more FASN inhibitors can be formulated into a pharmaceutically acceptable composition for administration to a mammal having fibrosis and/or a complication associated with fibrosis. For example, a therapeutically effective amount of a FASN inhibitor can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more FASN inhibitors can be designed for oral, parenteral (including subcutaneous, intramuscular, intravenous, and intradermal), or inhaled administration. When being administered orally, a pharmaceutical composition containing one or more FASN inhibitors can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. Compositions for inhalation can be delivered using, for example, an inhaler, a nebulizer, and/or a dry powder inhaler. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

In some cases, a pharmaceutically acceptable composition including one or more FASN inhibitors can be administered locally or systemically. For example, a composition containing a FASN inhibitor can be administered systemically by an oral administration to or inhalation by a mammal (e.g., a human).

Effective doses can vary depending on the severity of the fibrosis and/or complication associate with fibrosis, the route of administration, the age and general health condition of the subject, excipient usage, the possibility of co-usage with other therapeutic treatments such as use of other agents, and the judgment of the treating physician.

An effective amount of a composition containing one or more FASN inhibitors can be any amount that reduces the severity of a symptom of a condition being treated (e.g., a fibrosis and/or a complication associated with fibrosis) without producing significant toxicity to the mammal. For example, an effective amount of a FASN inhibitor such as C75 can be from about 0.3 mg/kg to about 50 mg/kg (e.g., from about 0.4 mg/kg to about 40 mg/kg, from about 0.5 mg/kg to about 30 mg/kg, from about 1 mg/kg to about 20 mg/kg, from about 2 mg/kg to about 15 mg/kg, or from about 3 mg/kg to about 10 mg/kg). The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., a fibrosis and/or a complication associated with fibrosis) may require an increase or decrease in the actual effective amount administered.

The frequency of administration can be any frequency that reduces the severity of a symptom of a condition to be treated (e.g., a fibrosis and/or a complication associated with fibrosis) without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition containing one or more FASN inhibitors can include rest periods. For example, a composition containing one or more FASN inhibitors can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., a fibrosis and/or a complication associated with fibrosis) may require an increase or decrease in administration frequency.

An effective duration for administering a composition containing one or more FASN inhibitors can be any duration that reduces the severity of a symptom of the condition to be treated (e.g., a fibrosis and/or a complication associated with fibrosis) without producing significant toxicity to the mammal. For example, the effective duration can vary from several days to several weeks, months, or years. In some cases, the effective duration for the treatment of a fibrosis and/or a complication associated with fibrosis can range in duration from about one month to about 10 years. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of one or more symptoms related to the condition being treated (e.g., a fibrosis and/or a complication associated with fibrosis) can be monitored. Any appropriate method can be used to determine whether or not the severity of a symptom is reduced. For example, the severity of a symptom of fibrosis can be assessed using imaging techniques (e.g., chest x-ray, CT scan, echocardiogram), lung function test (e.g., pulmonary function test, oximetry, exercise stress test), and/or tissue sample analysis (e.g., bronchoscopy, bronchoalveolar lavage, surgical biopsy) at different time points.

The invention will be further described in the following examples, which do not limit the scope of the invention described in the claims.

EXAMPLES

Example 1: FASN Expression in Mouse and Human Lung Tissues

Mice were treated with bleomycin to induce lung fibrosis or treated with saline as a control. Bleomycin-treated animals were treated dual-treated with lapatinib (an ErbB inhibitor) and imatinib (a PDGF receptor and cAbl inhibitor) to decrease lung fibrosis and stabilize peripheral blood oxygenation. Lungs were harvested and histological sections were prepared. Mouse lungs were stained with Masson's Trichrome (FIG. 1A), or FASN antibodies co-stained with hematoxylin (FIG. 1B). Color deconvoluted images of mouse lungs stained with FASN (FIG. 1C) indicate the area and intensity of FASN staining. Color-coded legend indicating intensity of FASN expression is provided.

Histological sections of normal and fibrotic lung tissues were stained with Masson's Trichrome (FIG. 1E), or FASN antibodies co-stained with Hematoxylin (FIG. 1F). Arrows indicate the magnified section showing fibroblasts found in normal human lung (FIGS. E-G top), or fibrotic foci observed in IPF (FIGS. E-G bottom). Color deconvoluted images are shown of FASN stained human lungs (Figure H). Color-coded legend indicating intensity of FASN expression is provided.

FASN expression was quantified in mouse and human lung tissues. FASN expression in mouse lung tissues was significantly greater in fibrosis versus normal (*p-value=0.021), or dual-treated lungs with imatinib+lapatinib (*p-value=0.025) (FIG. 1D). Mean values of mouse tissues analyzed per condition are indicated within each bar (n=3) and error bars show the standard error (FIG. 1D). FASN expression in human lung fibrotic foci was significantly greater than fibroblasts in normal human lung (*p-value=0.012) (FIG. 1H). Mean values of human cases are indicated within each bar (normal n=7; fibrotic n=12), and error bars show the standard error (FIG. 1H).

These results show that FASN expression correlates with lung fibrosis.

Example 2: TGFβ Regulates FASN Expression

Quiescent AKR-2B fibroblasts were stimulated in the absence or presence of TGFβ (10 ng/ml). Proteins and total RNA were obtained from treated and control cells. Protein samples were Western blotted for FASN or actin at the indicated times, and RNA samples (500 ng) were analyzed by RT-PCR using FASN primers. TGFβ stimulated FASN expression (FIG. 2A). TGFβ increased FASN transcription (FIG. 2B).

AKR-2B cultures were transiently transfected with wild-type FASN (FASN-luc) or mutant FASN promoter (FASN-Mut-luc) luciferase constructs and were treated with vehicle or TGFβ (10 ng/ml). Following 24 hours of treatment, normalized luciferase activity was determined. As shown in FIG. 2C, wild-type FASN exhibited significantly more luciferase activity than mutant FASN (n=3; **p-value<0.01).

Murine (AKR-2B and Swiss 3T3) and human (MRCS) lung fibroblast cells and primary human lung fibroblasts were stimulated for 24 hours in the absence or presence of 10 ng/ml TGFβ. Proteins were obtained from treated and control cells. Protein samples were Western blotted for FASN or GAPDH. TGFβ induced FASN expression in murine fibroblasts, human lung fibroblast cell lines, and primary lung fibroblasts (FIG. 2D).

These results show that TGFβ regulates FASN expression.

Example 3: FASN Induction by TGFβ

Figure 3B:
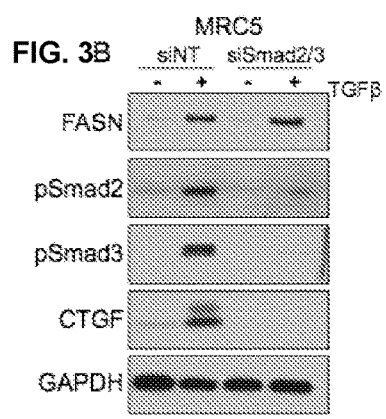

Murine fibroblasts (AKR-2B) and human lung fibroblasts (MRCS) were transfected with either a nontargeting control siRNA (60 nmol/L) or with Smad2/3-targeting siRNA (60 nmol/L). After 72 hours of cultivation, the transient transfectants were stimulated in the absence or presence of 10 ng/ml TGFβ for 24 hours. Proteins were obtained from treated and control cells. Protein samples were Western blotted for FASN, pSmad2, pSmad3, and connective tissue growth factor (CTGF), and Western blotted for GAPDH as a loading control. TGFβ induced FASN expression was independent of pSmad2/3 (FIGS. 3A and 3B).

Figure 3C:
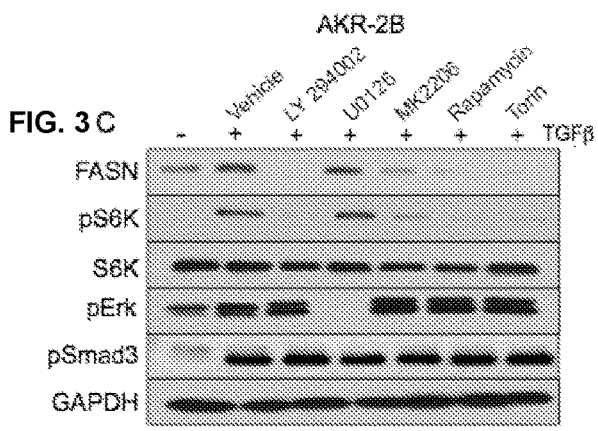
Figure 3D:
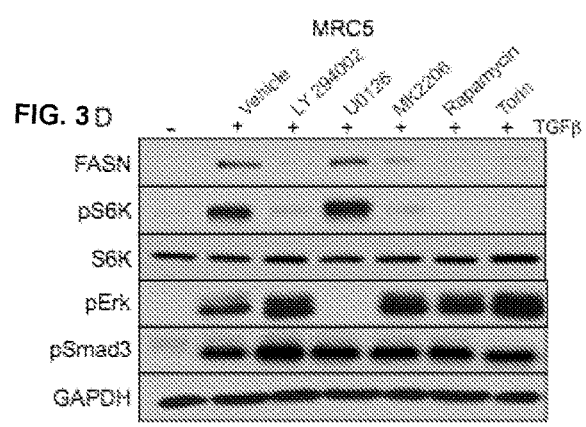

Murine fibroblasts (AKR-2B) and human lung fibroblasts (MRCS) were stimulated in the absence or presence of TGFβ (10 ng/ml) plus a PI3K inhibitor (LY294002; 10 μM), a MEK inhibitor (U0126; 10 μM), an AKT inhibitor (MK2206; 0.3 μM), a mTORC1 inhibitor (Rapamycin; 100 nM), or a mTORC1,2 inhibitor (Torin; 200 nM). Expression of pErk and pS6K/pS6K was determined at 1 and 6 hours post-stimulation while FASN, pSmad3, and GAPDH assessed at 24 hours. TGFβ induced FASN expression was abrogated in the presence of rapamycin or torin (FIGS. 3C and 3D).

Figure 3E:
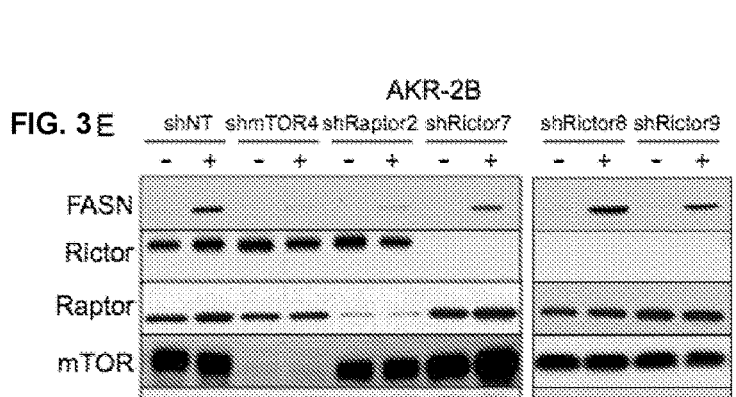

Murine fibroblasts (AKR-2B) transfected with either non-targeting (NT) short hairpin (sh) RNAs or shRNAs targeting mTOR, Raptor, or Rictor were treated in the absence or presence of 10 ng/ml TGFβ for 24 hours. Proteins were obtained from treated and control cells, and protein samples were Western blotted for FASN, Rictor, Raptor, mTor, and GAPDH (FIG. 3E).

These results show that FASN induction by TGFβ is independent of pSmad2/3 and mediated via mTORC1 signaling.

Example 4: FASN Activity and Profibrotic TGFβ Signaling

Figure 4A:
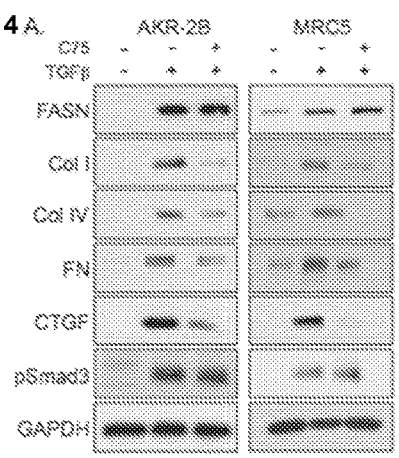
FIGS. 4A-4C show that FASN activity is required for profibrotic TGFβ signaling.

Murine fibroblasts (AKR-2B) and human lung fibroblasts (MRCS) were treated for 24 hours with vehicle (0.025% DMSO) or C75 (FASN inhibitor, 3 μM) in the presence or absence of TGFβ (10 ng/ml). Proteins were obtained from treated and control cells. Protein samples were Western blotted for FASN, Col I, Col IV, FN, CTGF, and pSmad3, and Western blotted for GAPDH as a loading control. TGFβ increased expression of FASN, Col I, Col IV, FN, CTGF, and pSmad3, but inhibition of FASN activity with C75 suppressed TGFβ induced Col I, Col IV, and FN expression (FIG. 4A).

Figure 4C:
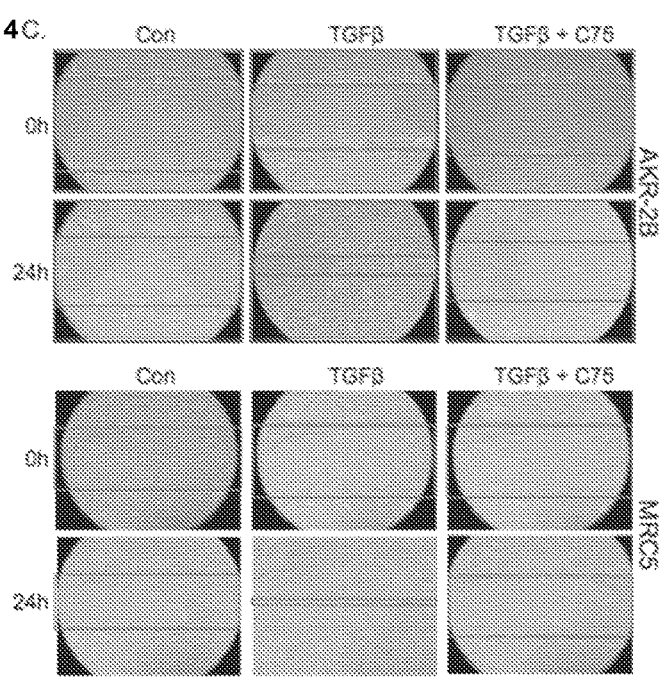
Figure 4B:
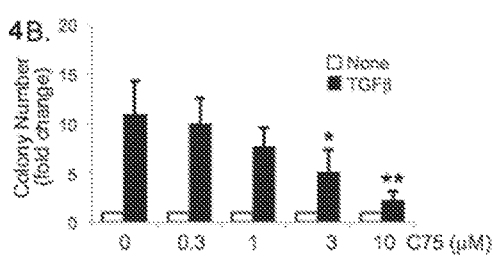

Murine fibroblasts (AKR-2B) were treated for 24 hours with vehicle (0.025% DMSO) or C75 (FASN inhibitor, 3 μM) in the presence or absence of TGFβ (10 ng/ml), and 0, 0.3, 1, 3, or 10 μM C75. Following 7 days growth, cells were subjected to soft agar colony formation assays. TGFβ increased colony formation, but inhibition of FASN activity with C75 suppressed TGFβ induced colony formation in a dose dependent manner (FIG. 4B; *p-value<0.05, **p-value<0.01). Data reflect the mean+/−standard deviation of triplicate wells from 3 experiments.

Murine fibroblasts (AKR-2B) and human lung fibroblasts (MRCS) were treated for 24 hours with vehicle (0.025% DMSO), TGFβ (10 ng/ml), or both TGFβ (10 ng/ml) and C75 (3 μM). Following 24 hours of treatment, culture plates were manually scratched. TGFβ increased cell migration, but inhibition of FASN activity with C75 suppressed TGFβ induced cell migration (FIG. 4C). Data are representative of 3 separate experiments.

These results show that FASN activity is required for profibrotic TGFβ signaling.

Example 5: Profibrotic TGFβ Signaling Induction of Fatty Acid Synthase

Figure 5A:
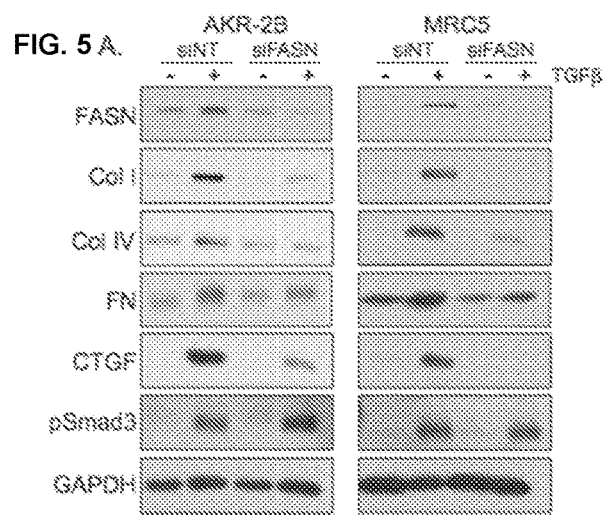
FIGS. 5A-5C shows that profibrotic TGFβ signaling is dependent upon the induction of fatty acid synthase.

Murine fibroblasts (AKR-2B) and human lung fibroblasts (MRCS) were transfected with either a nontargeting control siRNA (60 nmol/L) or with FASN-targeting siRNA (60 nmol/L). After 72 hours of cultivation, the transient transfectants were stimulated in the absence or presence of 10 ng/ml TGFβ for 24 hours. Proteins were obtained from treated and control cells. Protein samples were Western blotted for FASN, Col I, Col IV, FN, CTGF, and pSmad3, and Western blotted for GAPDH as a loading control. TGFβ increased expression of FASN, Col I, Col IV, FN, CTGF, and pSmad3, but inhibition of FASN activity with FASN-targeting siRNA suppressed TGFβ induced Col I, Col IV, and FN expression (FIG. 5A).

Figure 5B:
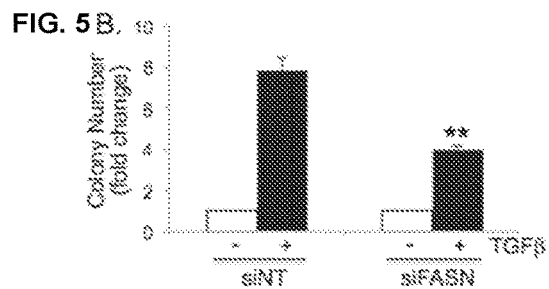

Murine fibroblasts (AKR-2B) were transfected with either a nontargeting control siRNA (60 nmol/L) or with FASN-targeting siRNA (60 nmol/L). After 72 hours of cultivation, the transient transfectants were stimulated in the absence or presence of 10 ng/ml TGFβ for 24 hours. Following 7 days growth, cells were subjected to soft agar colony formation assays. TGFβ increased colony formation, but inhibition of FASN activity with FASN-targeting siRNA suppressed TGFβ induced colony formation (FIG. 5B; **p-value<0.01). Data reflect the mean standard deviation of triplicate wells from 3 experiments.

Figure 5C:
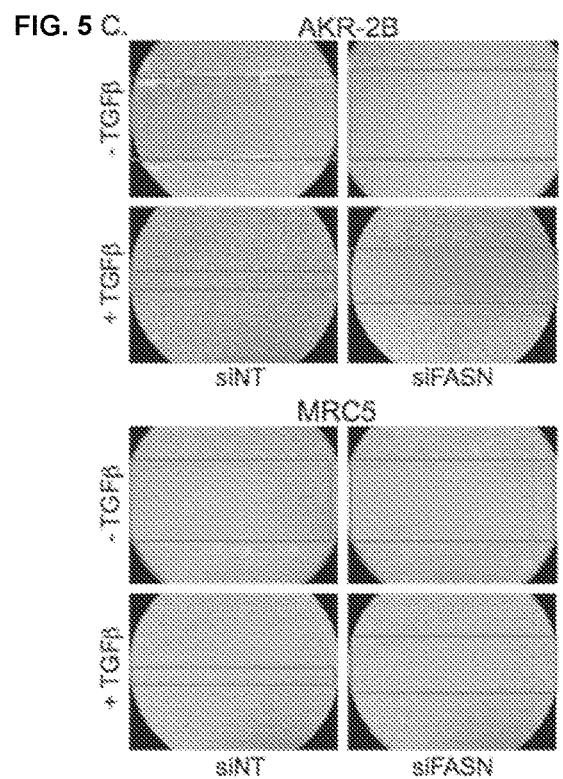

Murine (AKR-2B) lung fibroblasts were transfected with either a nontargeting control siRNA (60 nmol/L) or with FASN-targeting siRNA (60 nmol/L). After 72 hours of cultivation, the transient transfectants were stimulated in the absence or presence of 10 ng/ml TGFβ for 24 hours. Following 24 hours of treatment, culture plates were manually scratched. TGFβ increased cell migration, but inhibition of FASN activity with FASN-targeting siRNA suppressed TGFβ induced cell migration (FIG. 5C). Data are representative of 3 separate experiments.

These results show that profibrotic TGFβ signaling is dependent on FASN induction.

Example 6: Inhibition of FASN and Cell Proliferation

Figure 6A:
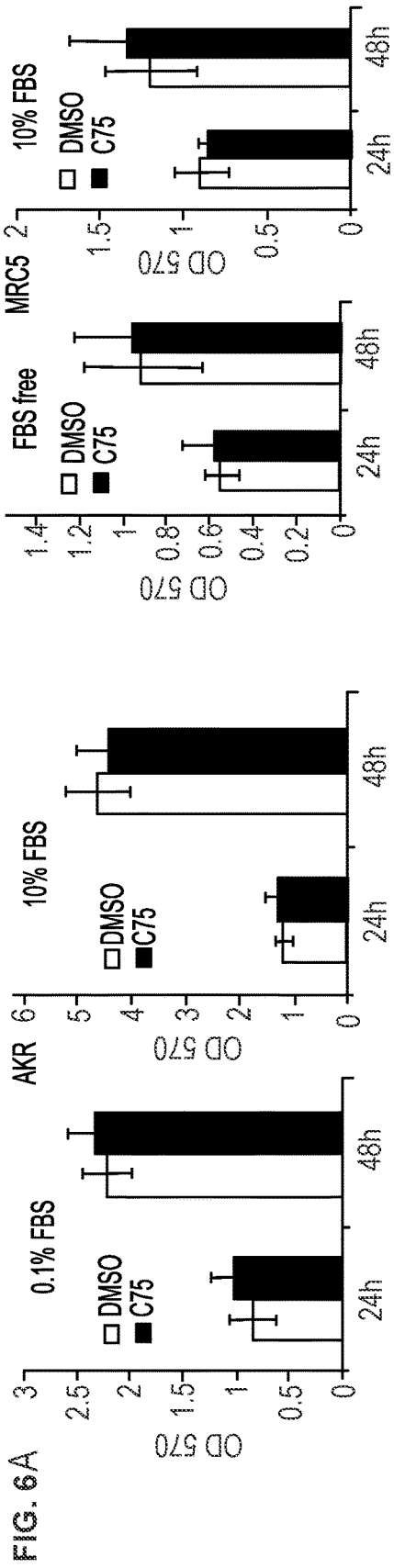
FIGS. 6A-6B contain graphs showing inhibition of FASN does not inhibit in vitro cell proliferation.
Figure 6B:
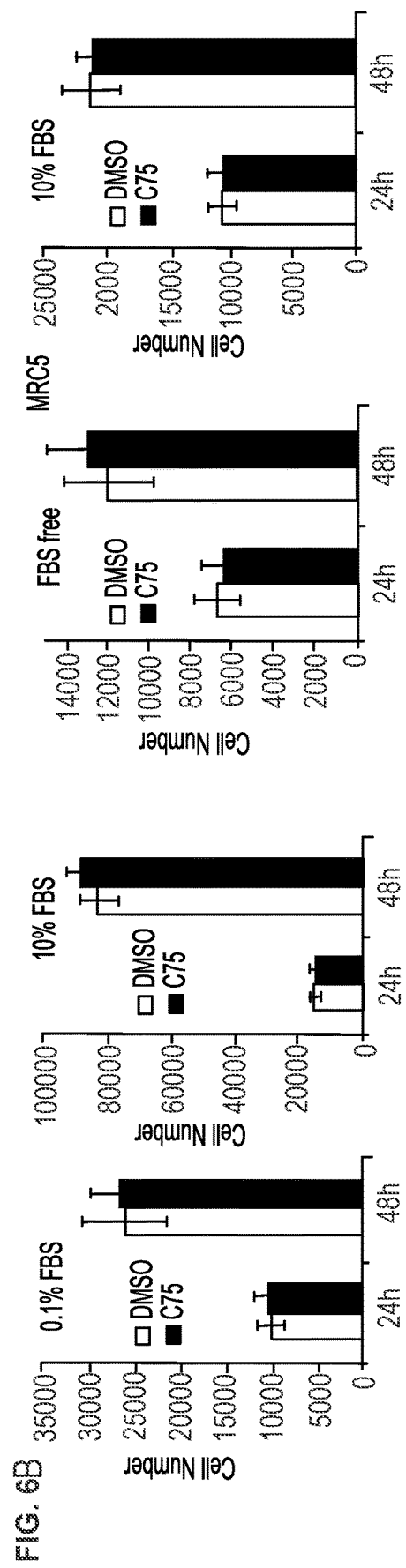
Figure 8:
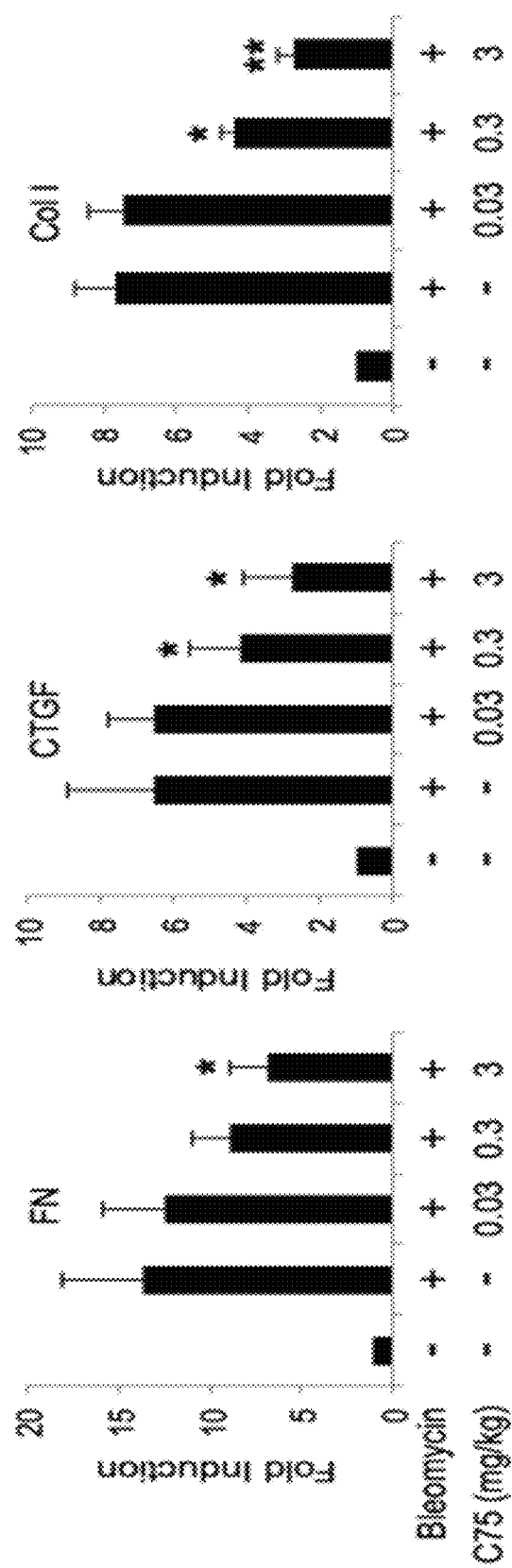
FIG. 8 includes graphs showing change in expression of fibronectin (FN), connective tissue growth factor (CTGF), and Collagen I (Col I) in murine lung tissue harvested on day 28 from mice challenged with bleomycin (+) or vehicle (−) and treated every 4th day with vehicle (−) or the indicated concentration (mg/kg) of C75 beginning 14 days following initial bleomycin insult; *p-value<0.05, **p-value<0.01.
Figure 9:
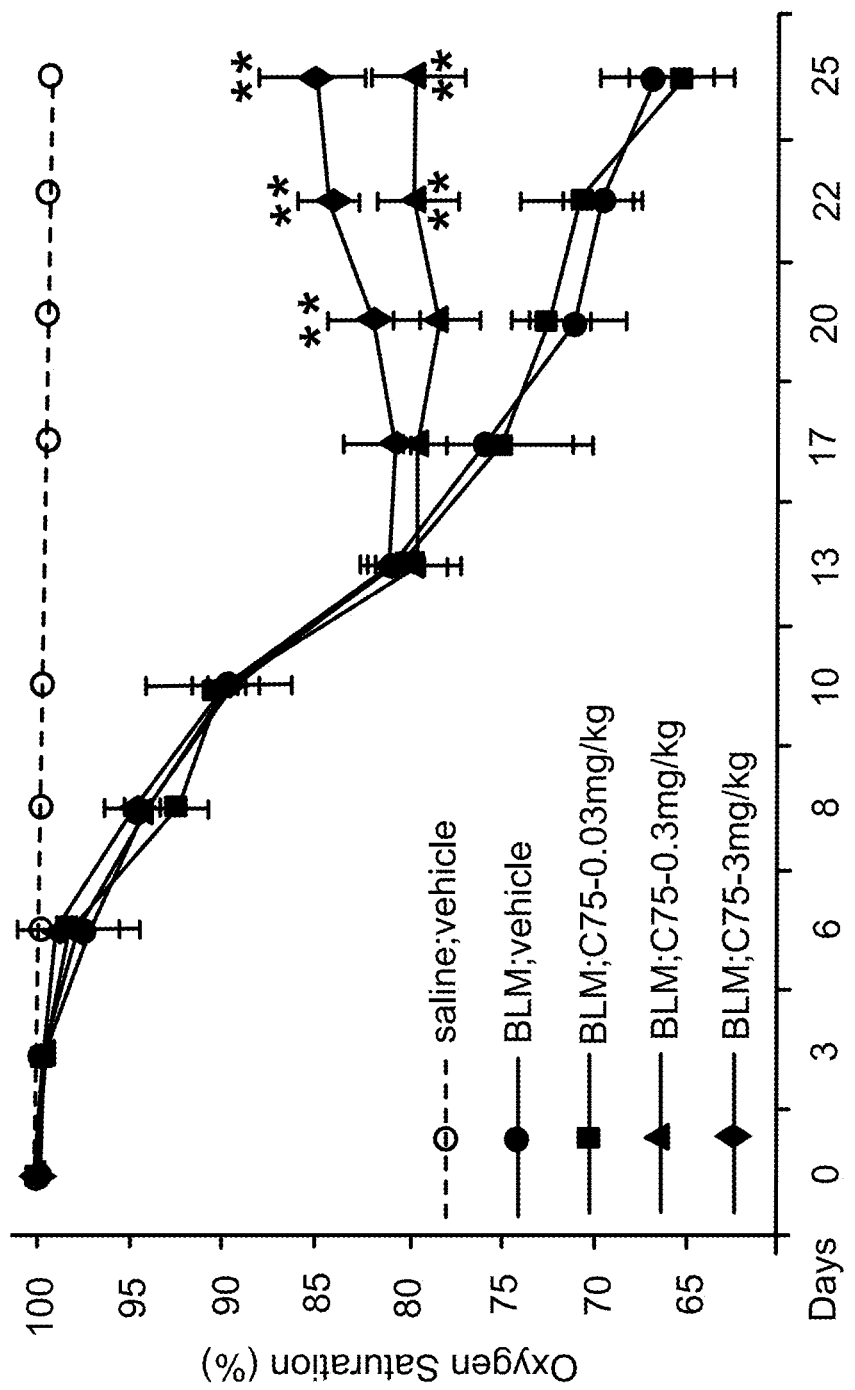
FIG. 9 is a graph showing oxygen saturation levels in mice challenged with bleomycin (BLM) or saline for 25 days and treated once every 4th day with vehicle or the indicated concentration (mg/kg) of C75 beginning 14 days after initial BLM insult; *p-value<0.05, **p-value<0.01.

Murine fibroblasts (AKR-2B) and human lung fibroblasts (MRCS) were seeded at $2.5 \times 10^3$ or $1 \times 10^4$ cells/96 well plate, respectively. AKR-2B cells were seeded in medium containing 10% DMEM/FBS, and MRCS cells were seeded in medium containing 10% EMEM/FBS. 24 hours after seeding, the medium was removed and replaced with DMEM or EMEM containing vehicle (0.1% DMSO), or C75 (3 μM) either in 10%, 0.1%, or 0% FBS for 24 hours prior to MTT assay (FIG. 6A). Absorbance was measured at 570 nm. Results represent mean±SEM from three independent experiments Murine fibroblasts (AKR-2B) and human lung fibroblasts (MRCS) were seeded at $1.0 \times 10^4$ cells/well in 24 well plates for 24 hours. AKR-2B cells were seeded in medium containing 10% DMEM/FBS, and MRCS cells were seeded in medium containing 10% EMEM/FBS. 24 hours after seeding, the medium was removed and replaced with DMEM or EMEM containing vehicle (0.1% DMSO), or C75 (3 μM) either in 10%, 0.1%, or 0% FBS for 24 hours prior to determining cell counts following an additional 24 hour and 48 hour incubation (FIG. 6B). Results represent mean±SEM from three independent experiments.

These results show that inhibition of FASN does not inhibit in vitro cell proliferation.

Example 7: Inhibition FASN and Liver Enzymes or Inflammatory Cell Recruitment

C57BL/6 mice were intratracheally treated with an equal volume of saline (control) or bleomycin (BLM; 0.075 U). On day 14 all animals began treatment every $4^{th}$ day with either vehicle (Methocel/saline) or 3.0 mg/kg of C75. Blood samples were obtained at days 0, 14, and 28 from the facial vein of unanesthetized animals and assessed for effect on liver enzymes. Serum levels (U/L, units per liter; g/dL, grams per deciliter) of alkaline phosphatase (ALP), alanine aminotransferase (ALT), and albumin were determined using a Piccolo Xpress Chemistry Analyzer (FIG. 7A). Data are presented as mean+/−SEM of n=5.

C57BL/6 mice were intratracheally treated with an equal volume of saline (control) or bleomycin (BLM; 0.075 U). On day 14 all animals began treatment every $4^{th}$ day with either vehicle (Methocel/saline) or 3.0 mg/kg of C75. Blood samples were obtained at days 0, 14, and 28 from the facial vein of unanesthetized animals and assessed for effect on inflammatory cells. Quantification of lymphocytes, monocytes, and neutrophils were measured using a VetScan HM5 Analyzer (FIG. 7B). Data are presented as mean+/−SEM of n=5.

These results show that inhibition of FASN has no demonstrable effect on murine liver enzymes or inflammatory cell recruitment.

Example 8: Inhibition of FASN and Lung Remodeling

Mice were challenged with bleomycin or vehicle (methocel/0.1% DMSO), and every $4^{th}$ day, beginning 14 days following initial bleomycin insult, were treated by intraperitoneal injection with vehicle, 0.03 mg/kg, 0.3 mg/kg, or 3 mg/kg C75. Murine lung tissue was harvested on day 28 and RNA was obtained. qPCR was performed using primers specific for FN, CTGF, and Col I.

Bleomycin-induced fibrotic conditions demonstrated increased FN, CTGF, and Col I expression, but inhibition of FASN activity with C75 reduced FN, CTGF, and Col I expression in a dose dependent manner (FIG. 6; *p-value<0.05, **p-value<0.01). Data reflect mean standard deviation from lungs of n=5 (control, bleomycin, 0.03 mg/kg C75), 7 (0.3 mg/kg C75), or 8 (3 mg/kg C75) animals.

These results show that FASN inhibition prevents profibrotic gene expression in lungs and that lung remodeling is attenuated by inhibiting FASN activity.

Example 9: Inhibition of FASN and Lung Gas Exchange

Mice were challenged with bleomycin or saline for 25 days, and every 4$^{th}$ day, beginning 14 days following initial bleomycin insult, were treated with vehicle (methocel/0.1% DMSO) or with 0.03 mg/kg, 0.3 mg/kg, or 3 mg/kg C75. Oxygen saturation ($SpO_2$) levels (determined on room air) were measured.

Bleomycin-induced fibrotic conditions caused reduced, time-dependent fluctuations in oxygen saturation, but inhibition of FASN activity with C75 stabilized lung gas exchange in a dose dependent manner (FIG. 7; *p-value<0.05, **p-value<0.01). Error bars reflect standard deviation from n=5 (control, BLM, 0.03 mg/kg C75), 7 (0.3 mg/kg C75), or 8 (3 mg/kg C75) animals.

These results show that FASN inhibition maintains/improves peripheral blood oxygenation.

Example 10: Inhibition FASN and Lung Function

Figure 10A:
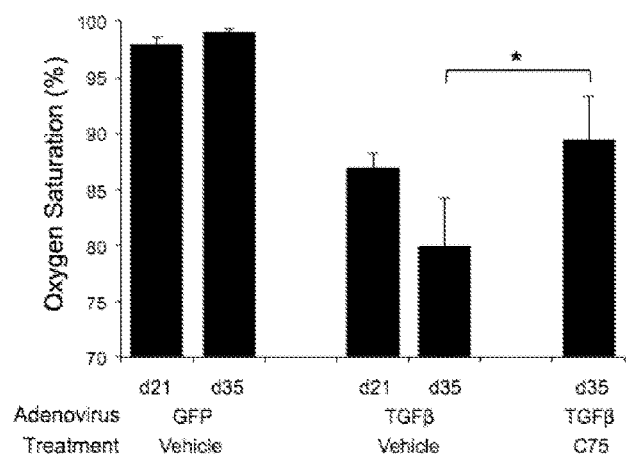
FIGS. 10A-10C contain graphs showing FASN inhibition stabilizes lung function in adenovirus-TGFβ model of pulmonary fibrosis.

Mice were infected with 1×10$^8$ pfu adenovirus particles expressing control (GFP) or active TGFβ1 by tracheal instillation. On day 21 all animals began treatment every 4$^{th}$ day with either vehicle (Methocel/saline) or 3.0 mg/kg of C75. Peripheral blood oxygen determined on days 21 and 35 (FIG. 10A). Data reflect mean+/−SEM of n=8 and n=15 for adenovirus-GFP and adenovirus-TGFβ, respectively. *P<0.05.

Figure 10B:
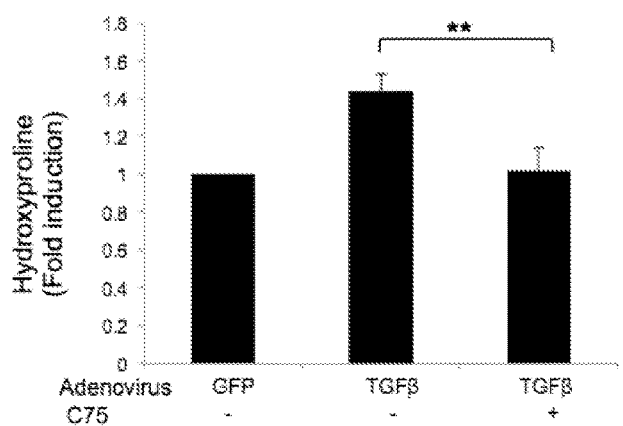
Figure 10C:
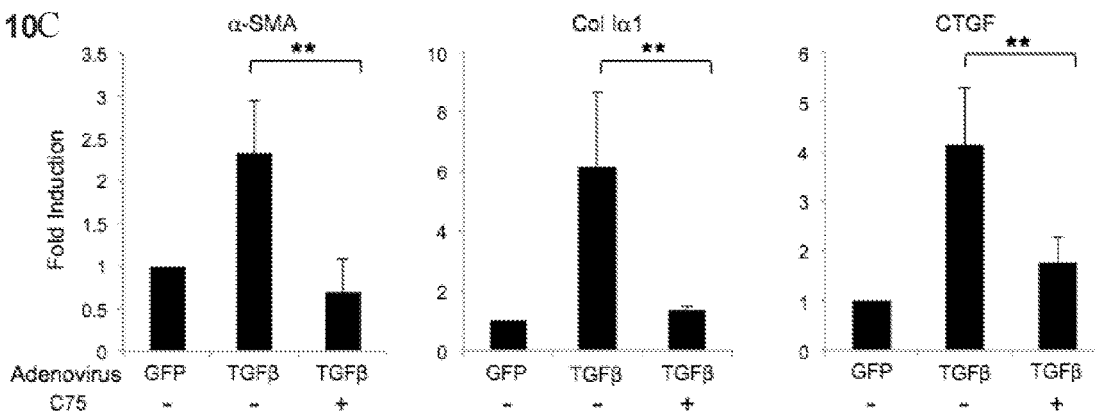

Mice were infected with 1×10$^8$ pfu adenovirus particles expressing control (GFP) or active TGFβ1 by tracheal instillation. On day 21 all animals began treatment every 4$^{th}$ day with either vehicle (Methocel/saline) or 3.0 mg/kg of C75. Mice were sacrificed on day 39 and processed for lung hydroxyproline content (FIG. 10B). Data reflect mean+/−SEM of n=8 and n=15 for adenovirus-GFP and adenovirus-TGFβ, respectively. **P<0.01.

Mice were infected with 1×10$^8$ pfu adenovirus particles expressing control (GFP) or active TGFβ1 by tracheal instillation. On day 21 all animals began treatment every 4$^{th}$ day with either vehicle (Methocel/saline) or 3.0 mg/kg of C75. Mice were sacrificed on day 39 and processed for qPCR expression of connective tissue growth factor (CTGF), alpha smooth muscle actin (α-SMA), and collagen Iα1 (Col Iα1). Data reflect mean+/−SEM of n=8 and n=15 for adenovirus-GFP and adenovirus-TGFβ, respectively. *P<0.05, **P<0.01.

These results show that inhibition of FASN stabilizes lung function in adenovirus-TGFβ model of pulmonary fibrosis.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for treating pulmonary fibrosis in a mammal, wherein said method comprises administering an inhibitor of fatty acid synthase activity to a mammal identified as having pulmonary fibrosis, thereby treating said pulmonary fibrosis, wherein said inhibitor is selected from the group consisting of C75 and TVB-2640.

2. The method of claim 1, wherein said mammal is a human.

3. The method of claim 1, wherein said pulmonary fibrosis is idiopathic pulmonary fibrosis.

4. The method of claim 1, wherein said inhibitor is C75.

5. The method of claim 1, wherein said inhibitor is TVB-2640.

* * * * *

UNITED STATES PATENT AND TRADEMARK OFFICE
CERTIFICATE OF CORRECTION

PATENT NO. : 12,280,036 B2
APPLICATION NO. : 17/673518
DATED : April 22, 2025
INVENTOR(S) : Edward B. Leof et al.

Page 1 of 1

It is certified that error appears in the above-identified patent and that said Letters Patent is hereby corrected as shown below:

In the Specification

In Column 1, Line 8 (Approx.), delete "2018," and insert -- 2018 (abandoned), --.

Signed and Sealed this
First Day of July, 2025

Coke Morgan Stewart
*Acting Director of the United States Patent and Trademark Office*